US008682486B2

(12) United States Patent
Wang et al.

(10) Patent No.: US 8,682,486 B2
(45) Date of Patent: *Mar. 25, 2014

(54) MEDICAL TELE-ROBOTIC SYSTEM WITH A MASTER REMOTE STATION WITH AN ARBITRATOR

(71) Applicant: InTouch Technologies, Inc., Goleta, CA (US)

(72) Inventors: Yulun Wang, Goleta, CA (US); Charles S. Jordan, Santa Barbara, CA (US); Keith Phillip Laby, Santa Barbara, CA (US); Jonathan Southard, Santa Barbara, CA (US)

(73) Assignee: InTouch Technologies, Inc., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/944,526

(22) Filed: Jul. 17, 2013

(65) Prior Publication Data

US 2013/0304257 A1 Nov. 14, 2013

Related U.S. Application Data

(63) Continuation of application No. 11/983,058, filed on Nov. 5, 2007, now Pat. No. 8,515,577, which is a continuation of application No. 10/783,760, filed on Feb. 20, 2004, now abandoned, which is a continuation-in-part of application No. 10/206,457, filed on Jul. 25, 2002, now Pat. No. 6,925,357.

(60) Provisional application No. 60/449,762, filed on Feb. 24, 2003.

(51) Int. Cl.
*G05B 19/04* (2006.01)
*G05B 19/418* (2006.01)

(52) U.S. Cl.
USPC ............... 700/247; 700/13; 700/90; 700/245; 700/248; 700/257; 700/259; 700/260; 700/261; 700/262; 700/264

(58) Field of Classification Search
USPC ............. 700/13, 90, 264, 248, 245, 247, 251, 700/257, 258, 260, 261, 262; 901/1, 14, 46; 348/14.01–14.09, 14.11, 14.12, 14.13; 709/203, 204
See application file for complete search history.

(56) References Cited

U.S. PATENT DOCUMENTS 4,679,152 A   7/1987  Perdue
4,766,581 A * 8/1988  Korn et al. ............... 369/30.4
(Continued)

FOREIGN PATENT DOCUMENTS

AU   2000/0012162 A   10/1999
EP   2003/1304872 A1   4/2003
(Continued)

OTHER PUBLICATIONS

"Appeal from the United States District Court for the Central District of California in case No. 11-cv-9185, Judge Percy Anderson, Joint Appendix, vol. I of IV (pp. A1-A6357)", Jun. 24, 2013, 549 pgs.

(Continued)

*Primary Examiner* — Khoi Tran
*Assistant Examiner* — Jorge Peche
(74) *Attorney, Agent, or Firm* — Chris Lambrecht

(57) ABSTRACT

A robotic system that includes a mobile robot linked to a plurality of remote stations. One of the remote stations includes an arbitrator that controls access to the robot. Each remote station may be assigned a priority that is used by the arbitrator to determine which station has access to the robot. The arbitrator may include notification and call back mechanisms for sending messages relating to an access request and a granting of access for a remote station.

12 Claims, 10 Drawing Sheets

(56) References Cited

U.S. PATENT DOCUMENTS

| | | | |
|---|---|---|---|
| 4,942,512 A * | 7/1990 | Kohno | 700/4 |
| 5,157,491 A * | 10/1992 | Kassatly | 348/14.08 |
| 5,230,023 A * | 7/1993 | Nakano | 381/110 |
| 5,673,082 A | 9/1997 | Wells et al. | |
| 5,758,079 A | 5/1998 | Ludwig et al. | |
| 5,787,545 A | 8/1998 | Colens | |
| 5,983,263 A | 11/1999 | Rothrock et al. | |
| 6,113,343 A | 9/2000 | Goldenberg et al. | |
| 6,160,582 A | 12/2000 | Hill | |
| 6,256,556 B1 * | 7/2001 | Zenke | 700/245 |
| 6,321,137 B1 * | 11/2001 | De Smet | 700/245 |
| 6,327,516 B1 | 12/2001 | Zenke | |
| 6,400,378 B1 | 6/2002 | Snook | |
| 6,445,964 B1 | 9/2002 | White et al. | |
| 6,480,762 B1 | 11/2002 | Uchikubo et al. | |
| 6,523,629 B1 * | 2/2003 | Buttz et al. | 180/167 |
| 6,763,282 B2 | 7/2004 | Glenn et al. | |
| 6,804,580 B1 | 10/2004 | Stoddard et al. | |
| 6,852,107 B2 * | 2/2005 | Wang et al. | 606/1 |
| 6,925,357 B2 * | 8/2005 | Wang et al. | 700/245 |
| 7,007,235 B1 | 2/2006 | Hussein et al. | |
| 7,142,947 B2 * | 11/2006 | Wang et al. | 700/264 |
| 7,158,860 B2 * | 1/2007 | Wang et al. | 700/245 |
| 7,158,861 B2 | 1/2007 | Wang et al. | |
| 7,164,970 B2 * | 1/2007 | Wang et al. | 700/245 |
| 7,202,851 B2 | 4/2007 | Cunningham et al. | |
| 7,346,429 B2 * | 3/2008 | Goldenberg et al. | 700/245 |
| 7,391,432 B2 | 6/2008 | Terada | |
| 7,421,470 B2 | 9/2008 | Ludwig et al. | |
| 7,433,921 B2 | 10/2008 | Ludwig et al. | |
| 7,643,051 B2 | 1/2010 | Sandberg et al. | |
| 7,647,320 B2 | 1/2010 | Mok et al. | |
| 7,831,575 B2 * | 11/2010 | Trossell et al. | 707/705 |
| 7,860,680 B2 | 12/2010 | Arms et al. | |
| 7,890,382 B2 | 2/2011 | Robb et al. | |
| 7,949,616 B2 | 5/2011 | Levy et al. | |
| 7,987,069 B2 | 7/2011 | Rodgers et al. | |
| 8,180,486 B2 | 5/2012 | Saito et al. | |
| 8,292,807 B2 | 10/2012 | Perkins et al. | |
| 8,340,654 B2 | 12/2012 | Bratton et al. | |
| 2001/0048464 A1 | 12/2001 | Barnett | |
| 2002/0033880 A1 | 3/2002 | Sul et al. | |
| 2002/0085030 A1 | 7/2002 | Ghani | |
| 2002/0095239 A1 | 7/2002 | Wallach et al. | |
| 2002/0109770 A1 | 8/2002 | Terada | |
| 2002/0133062 A1 | 9/2002 | Arling et al. | |
| 2003/0021107 A1 | 1/2003 | Howell et al. | |
| 2003/0050734 A1 | 3/2003 | Lapham | |
| 2003/0126361 A1 * | 7/2003 | Slater et al. | 711/114 |
| 2003/0152145 A1 | 8/2003 | Kawakita | |
| 2003/0220715 A1 * | 11/2003 | Kneifel et al. | 700/248 |
| 2004/0095516 A1 | 5/2004 | Rohlicek | |
| 2004/0107254 A1 | 6/2004 | Ludwig et al. | |
| 2004/0107255 A1 | 6/2004 | Ludwig et al. | |
| 2004/0123158 A1 * | 6/2004 | Roskind | 713/202 |
| 2004/0172306 A1 | 9/2004 | Wohl et al. | |
| 2004/0222638 A1 | 11/2004 | Bednyak | |
| 2004/0240981 A1 * | 12/2004 | Dothan et al. | 414/795.4 |
| 2005/0004078 A1 | 1/2005 | Goldenberg et al. | |
| 2005/0013149 A1 * | 1/2005 | Trossell | 365/1 |
| 2005/0060211 A1 | 3/2005 | Xiao et al. | |
| 2005/0078816 A1 | 4/2005 | Sekiguchi et al. | |
| 2005/0125098 A1 | 6/2005 | Wang et al. | |
| 2005/0234592 A1 | 10/2005 | McGee et al. | |
| 2006/0020694 A1 | 1/2006 | Nag et al. | |
| 2006/0074719 A1 | 4/2006 | Horner | |
| 2006/0125356 A1 | 6/2006 | Meek et al. | |
| 2006/0173708 A1 | 8/2006 | Vining et al. | |
| 2006/0178777 A1 * | 8/2006 | Park et al. | 700/245 |
| 2006/0224781 A1 | 10/2006 | Tsao et al. | |
| 2006/0271238 A1 * | 11/2006 | Choi et al. | 700/245 |
| 2006/0271400 A1 | 11/2006 | Clements et al. | |
| 2007/0025711 A1 | 2/2007 | Marcus | |
| 2007/0255706 A1 | 11/2007 | Iketani et al. | |
| 2008/0009969 A1 | 1/2008 | Bruemmer et al. | |
| 2008/0201016 A1 | 8/2008 | Finlay | |
| 2008/0306375 A1 | 12/2008 | Sayler et al. | |
| 2009/0044334 A1 | 2/2009 | Parsell et al. | |
| 2009/0164255 A1 | 6/2009 | Menschik et al. | |
| 2009/0171170 A1 | 7/2009 | Li et al. | |
| 2009/0177323 A1 | 7/2009 | Ziegler et al. | |
| 2009/0177641 A1 | 7/2009 | Raghavan | |
| 2009/0248200 A1 | 10/2009 | Root | |
| 2010/0051596 A1 | 3/2010 | Diedrick et al. | |
| 2010/0063848 A1 | 3/2010 | Kremer et al. | |
| 2010/0145479 A1 | 6/2010 | Griffiths | |
| 2010/0228249 A1 | 9/2010 | Mohr et al. | |
| 2011/0213210 A1 | 9/2011 | Temby et al. | |
| 2012/0036484 A1 | 2/2012 | Zhang et al. | |
| 2012/0095352 A1 | 4/2012 | Tran | |
| 2012/0191246 A1 | 7/2012 | Roe et al. | |

FOREIGN PATENT DOCUMENTS

| | | |
|---|---|---|
| EP | 2007/1763243 A2 | 3/2007 |
| JP | 2006/508806 A | 3/2006 |
| JP | 2006/109094 A | 4/2006 |
| WO | 00/25516 A1 | 5/2000 |

OTHER PUBLICATIONS

"Appeal from the United States District Court for the Central District of California in case No. 11-cv-9185, Judge Percy Anderson, Joint Appendix, vol. II of IV (pp. A6849-A10634)", Jun. 24, 2013, 479 pgs.

"Appeal from the United States District Court for the Central District of California in case No. 11-cv-9185, Judge Percy Anderson, Joint Appendix, vol. III of IV (pp. A10654-A15517)", Jun. 24, 2013, 548 pgs.

"Appeal from the United States District Court for the Central District of California in case No. 11-cv-9185, Judge Percy Anderson, Joint Appendix, vol. IV of IV (pp. A15677-A18127)", Jun. 24, 2013, 406 pgs.

Apple, Inc., "iPhone", iPhone Series, XP002696350, http://en.wikipedia.org/wiki/IPhone_5, n. d., retrieved Apr. 30, 2013, pp. 1-29.

Blaer, et al., "TopBot: Automated Network Topology Detection With a Mobile Robot", Proceedings of the 2003 IEEE International Conference on Robotics 7 Automation, Taipei, Taiwan, Sep. 14-19, 2003, pp. 1582-1587.

Bradner, "The Internet Standards Process—Revision 3", Network Working Group Request for Comments: 2026, www.rfc-e ditor.org?rfC/rfc2026. txt, Oct. 1996, pp. 1-36.

"Brief for Defendant-Appellee VGO Communications, Inc., Appeal from the United States District Court for the Central District of California, in Case No. 2:11-cv-9185, Judge Percy Anderson", May 28, 2013. 75 pgs.

Christensen et al., "BeeSoft User's Guide and Reference", Robots for the Real World™, Real World Interface, Inc., www.praecogito.com./-brudy/zaza/BeeSoft-manual-1.2-2/ beeman~1.htm, Sep. 26, 1997, pp. 1-203.

"Civil Minutes-General: Case No. CV 11-9185PA (AJWx), InTouch Tech., Inc. v. VGo Commc'ns, Inc.", Sep. 10, 2012. 7 pgs.

Dario, "A Robot Workstation for Diagnosis and Physical Therapy", IEEE Catalog No. 88TH0234-5, 1989, pp. 67-72.

"Defendant-Counterclaimant VGO Communications, Inc.'s Memorandum of Points and Authorities in Support of Defendant-Counterclaimant VGO Communications, Inc.'s Motion for Summary Judgment of Invalidity of the Patents-In-Suit", Sep. 10, 2012, 30 pgs.

Gostai, "Robotic Telepresence: Gostai Jazz", Flyer, http://www.gostai.com, n. date, 4 pgs.

Leifer, et al., "VIPRR: A Virtually in Person Rehabilitation Robot", Proceedings of 1997 International Conference on Rehabilitation Robotics, http://www.stanford.edu/group/rrdlPeople/vdl/publicationsIICORR97IVIPRR.html, Apr. 14-15, 1997, 4 pgs.

Minsky "Telepresence", OMNI, Jun. 1980, pp. 1-6.

Motorola Technical Developments, et al., "Detection of Target Mobile Signal Strength", PriorArt Database: Technical Disclosure, IP.com, Retrieved from http:www.ip.com/pubview/

(56) References Cited

OTHER PUBLICATIONS

IPCOM000009024D, original publication date: Jan. 1, 1999 by Motorola, Inc., pp. 205-206, Aug. 1, 2002, pp. 1583-1587.

Noritsugu, "Application of Rubber Artificial Muscle Manipulator as a Rehabilitation Robot", IEEE/ASME Transations on Mechatronics, vol. 2, No. 4, Dec. 1997, pp. 259-267.

"Opening Brief for Plaintiff-Appellant InTouch Technologies, Inc., Appeal from the United States District Court for the Central District of California in case No. 11-cv-9185, Judge Percy Anderson", Apr. 12, 2013, 187 pgs.

Osborn, "QoLT Research Overview", Quality of Life Technology Center:A National Science Foundation Engineering Research Center, Carnegie Mellon University of Pittsburgh, www.qolt.org, n. date, 2 pgs.

"Reply Brief for Plaintiff-Appellant InTouch Technologies, Inc., Appeal from the United States District Court for the Central District of California in case No. 11-cv-9185, Judge Percy Anderson", Jun. 14, 2013, 39 pgs.

Reynolds et al., "Review of Robotic Telemedicine Utilization in Intensive Care Units (ICUs)", 11th Annual ATA Symposium, Tampa, Florida, 2011, 1 pg.

"Saphira Software Manual", Saphira Version 5.3, ActiveMedia, Inc., 1997, 105 pgs.

Tipsuwan, et al., "Gain Adaptation of Networked Mobile Robot to Compensate QoS Deterioration", IEEE, 2000, pp. 3146-3151.

Tsui, at al., "Exploring Use Cases for Telepresence Robots", Human-Robot Interaction, Lausanne, Switzerland, http://robotics.cs.uml.edu/fileadmin/content/publications/2011/tsui-et-al-telepresence-HRI11.pdf, Robotics Lab UMass Lowell, 2011, 7 pgs.

UMASS Lowell Robotics Lab, "Robotics Lab @ UMASS Lowell", Brochure, http://robotics.cs.uml.edu/fileadmin/content/brochures/roboticslab_brochure_2011_WEB.pdf, 2011, 2 pgs.

Video Middleware Group, "H.350 Directory Services for Multimedia", http://www.vide.net/resources/h350vendor.pdf, n. date, 2 pgs.

* cited by examiner

MEDICAL TELE-ROBOTIC SYSTEM WITH A MASTER REMOTE STATION WITH AN ARBITRATOR

CROSS REFERENCE TO RELATED APPLICATIONS

This application is a continuation of application Ser. No. 11/983,058, pending, which is a continuation of Ser. No. 10/783,760 filed Feb. 20, 2004, abandoned, which is a continuation-in-part of application Ser. No. 10/206,457 filed on Jul. 25, 2002, now U.S. Pat. No. 6,925,357 granted on Aug. 2, 2005, and claims priority to Provisional Application No. 60/449,762 filed on Feb. 24, 2003.

BACKGROUND OF THE INVENTION

1. Field of the Invention

The subject matter disclosed generally relates to the field of robotics.

2. Background Information

There is a growing need to provide remote health care to patients that have a variety of ailments ranging from Alzheimers to stress disorders. To minimize costs it is desirable to provide home care for such patients. Home care typically requires a periodic visit by a health care provider such as a nurse or some type of assistant. Due to financial and/or staffing issues the health care provider may not be there when the patient needs some type of assistance. Additionally, existing staff must be continuously trained, which can create a burden on training personnel. It would be desirable to provide a system that would allow a health care provider to remotely care for a patient without being physically present.

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope which has a camera that allows a surgeon to view a surgical area of a patient.

Tele-robots such as hazardous waste handlers and bomb detectors may contain a camera that allows the operator to view the remote site. Canadian Pat. No. 2289697 issued to Treviranus, et al. discloses a teleconferencing platform that has both a camera and a monitor. The platform includes mechanisms to both pivot and raise the camera and monitor. The teleconferencing platform disclosed in the Canadian patent is stationary and cannot move about a building.

Publication Application No. US-2003-0050233-A1 discloses a remote robotic system wherein a plurality of remote stations can control a plurality of robotic arms used to perform a minimally invasive medical procedure. Each remote station can receive a video image provided by the endoscope inserted into the patient. The remote stations are linked to the robotic system by a dedicated communication link.

BRIEF SUMMARY OF THE INVENTION

A robotic system that includes a mobile robot coupled to a first remote station and a second remote station. The second remote station includes an arbitrator that controls access to the robot. The robot includes a camera and a monitor.

DETAILED DESCRIPTION

Disclosed is a robotic system that includes a mobile robot linked to a plurality of remote stations. One of the remote stations includes an arbitrator that controls access to the robot. Each remote station may be assigned a priority that is used by the arbitrator to determine which station has access to the robot. The arbitrator may include notification and call back mechanisms for sending messages relating to an access request and a granting of access for a remote station.

Figure 1:
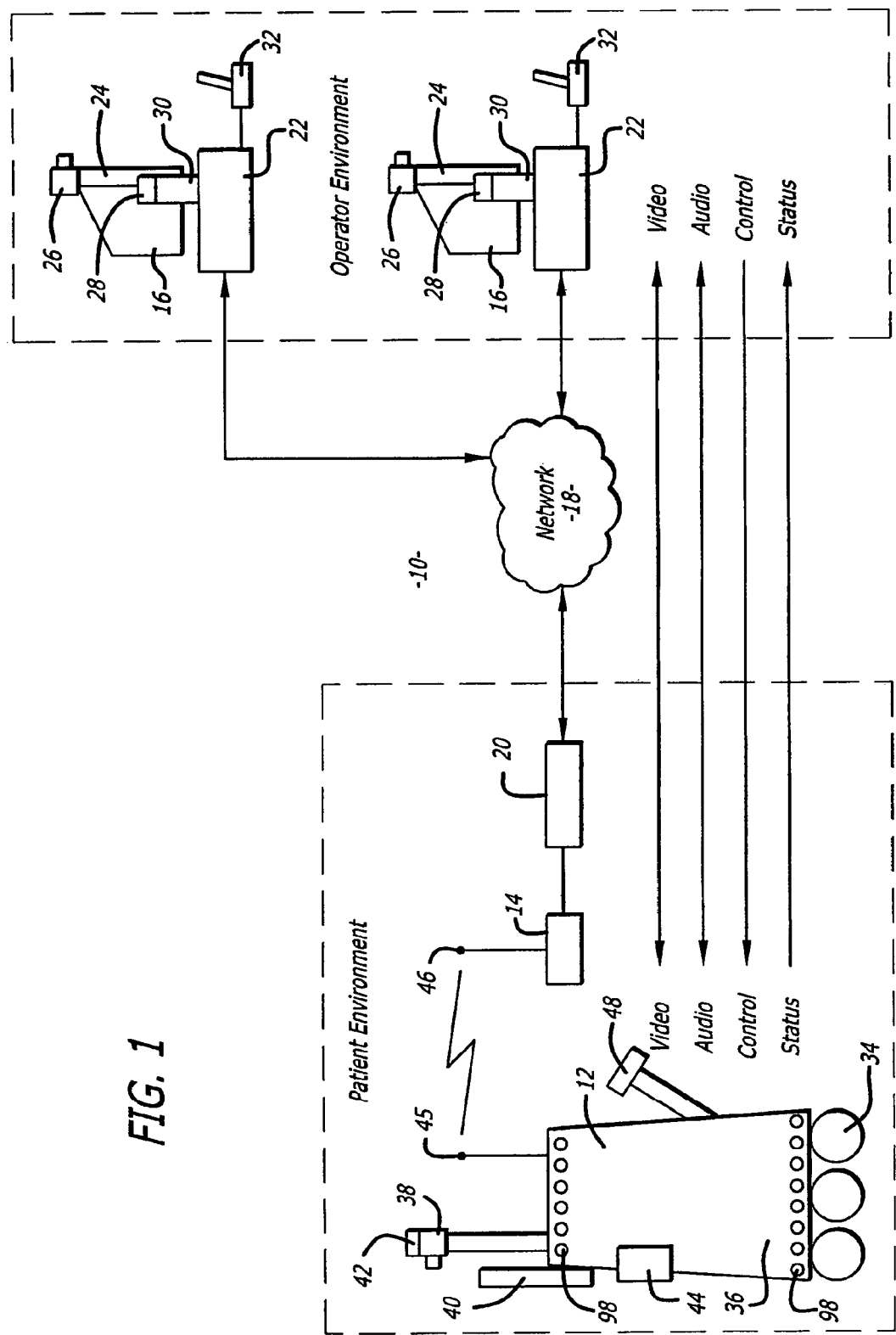
FIG. 1 is an illustration of a robotic system.

Referring to the drawings more particularly by reference numbers, FIG. 1 shows a robotic system 10. The robotic system 10 includes a robot 12, a base station 14 and a plurality of remote control stations 16. Each remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device.

Each remote control station 16 may include a computer 22 that has a monitor 24, a camera 26, a microphone 28 and a speaker 30. The computer 22 may also contain an input device 32 such as a joystick or a mouse. Each control station 16 is typically located in a place that is remote from the robot 12. Although only one robot 12 is shown, it is to be understood that the system 10 may have a plurality of robots 12. In general any number of robots 12 may be controlled by any number of remote stations. For example, one remote station 16 may be coupled to a plurality of robots 12, or one robot 12 may be coupled to a plurality of remote stations 16.

The robot 12 includes a movement platform 34 that is attached to a robot housing 36. Also attached to the robot housing 36 are a camera 38, a monitor 40, a microphone(s) 42 and a speaker 44. The microphone 42 and speaker 30 may create a stereophonic sound. The robot 12 may also have an antenna 45 that is wirelessly coupled to an antenna 46 of the base station 14. The system 10 allows a user at the remote control station 16 to move the robot 12 through the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user. The robot 12 may further have a handle 48 that can be rotated to a down position which allows someone to manually push or pull the robot 12.

Each remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

Figure 2:
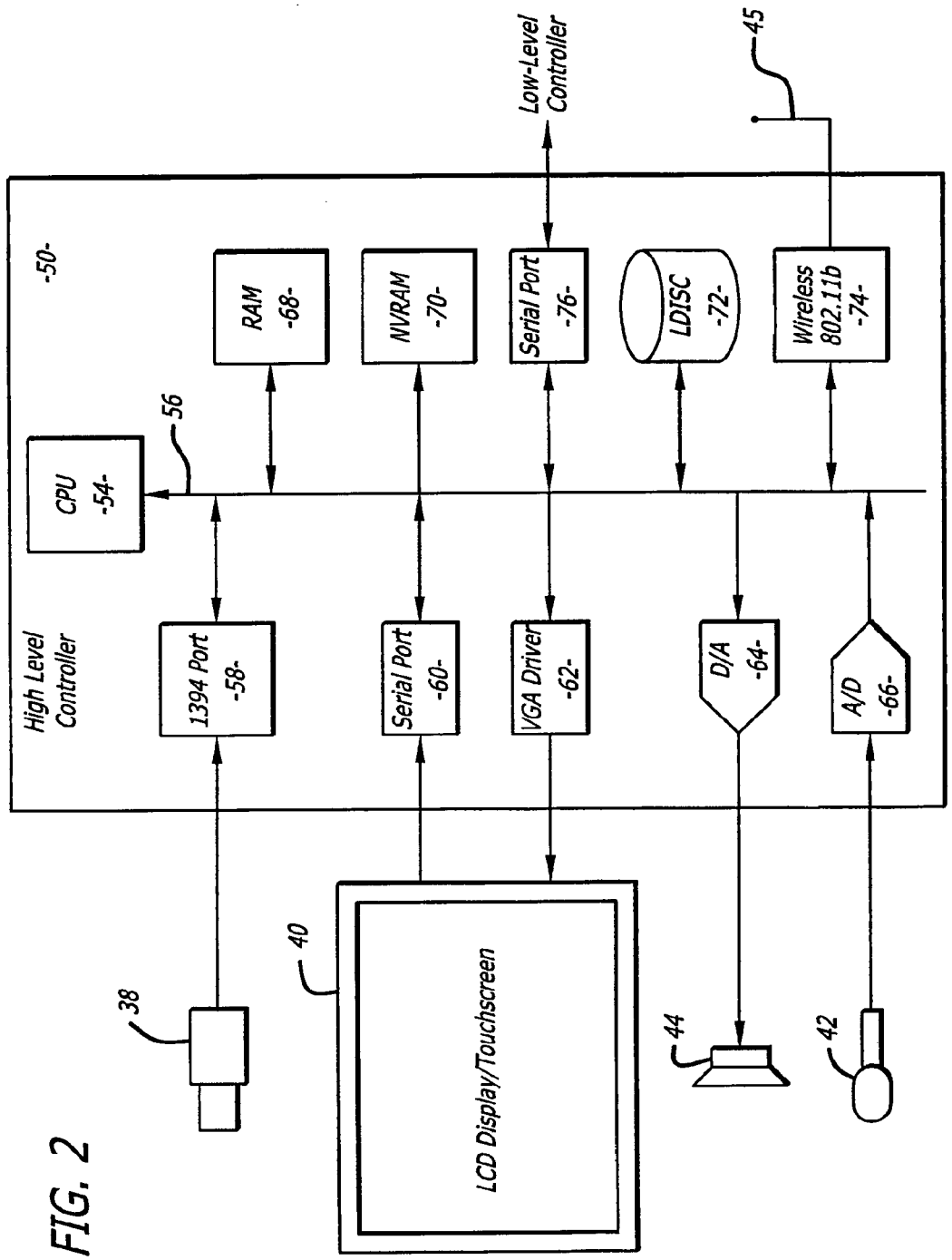
FIG. 2 is a schematic of an electrical system of a robot.
Figure 3:
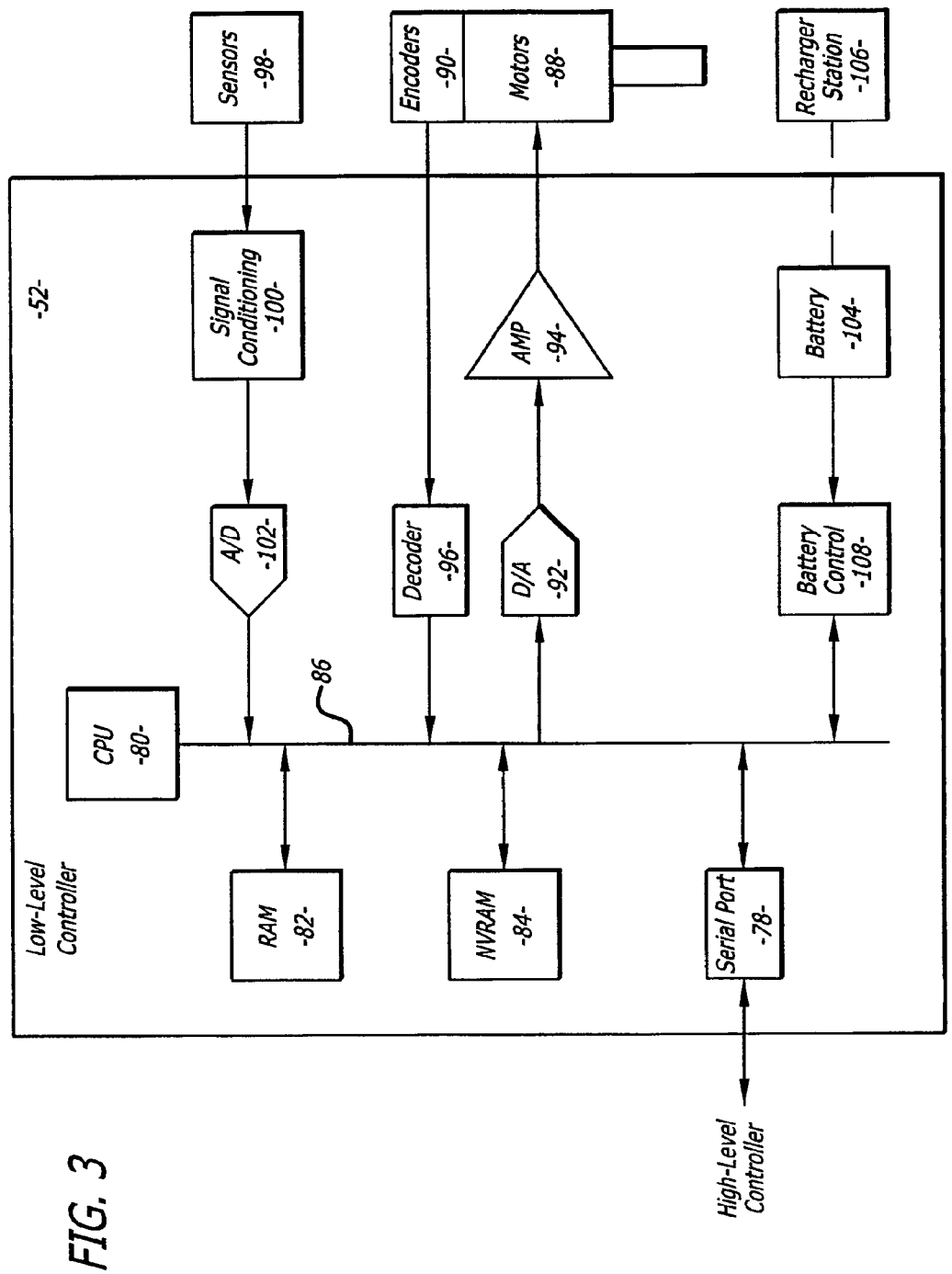
FIG. 3 is a further schematic of the electrical system of the robot.

FIGS. 2 and 3 show an embodiment of the robot 12. The robot 12 may include a high level control system 50 and a low level control system 52. The high level control system 50 may include a processor 54 that is connected to a bus 56. The bus is coupled to the camera 38 by an input/output (I/O) port 58, and to the monitor 40 by a serial output port 60 and a VGA driver 62. The monitor 40 may include a touchscreen function that allows the patient to enter input by touching the monitor screen.

The speaker 44 is coupled to the bus 56 by a digital to analog converter 64. The microphone 42 is coupled to the bus 56 by an analog to digital converter 66. The high level controller 50 may also contain random access memory (RAM) device 68, a non-volatile RAM device 70 and a mass storage device 72 that are all coupled to the bus 62. The mass storage device 72 may contain medical files of the patient that can be accessed by the user at the remote control station 16. For example, the mass storage device 72 may contain a picture of the patient. The user, particularly a health care provider, can recall the old picture and make a side by side comparison on the monitor 24 with a present video image of the patient provided by the camera 38. The robot antennae 45 may be coupled to a wireless transceiver 74. By way of example, the transceiver 74 may transmit and receive information in accordance with IEEE 802.11b.

The controller 54 may operate with a LINUX OS operating system. The controller 54 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control the communication between the robot 12 and the remote control station 16.

The high level controller 50 may be linked to the low level controller 52 by serial ports 76 and 78. The low level controller 52 includes a processor 80 that is coupled to a RAM device 82 and non-volatile RAM device 84 by a bus 86. The robot 12 contains a plurality of motors 88 and motor encoders 90. The encoders 90 provide feedback information regarding the output of the motors 88. The motors 88 can be coupled to the bus 86 by a digital to analog converter 92 and a driver amplifier 94. The encoders 90 can be coupled to the bus 86 by a decoder 96. The robot 12 also has a number of proximity sensors 98 (see also FIG. 1). The position sensors 98 can be coupled to the bus 86 by a signal conditioning circuit 100 and an analog to digital converter 102.

The low level controller 52 runs software routines that mechanically actuate the robot 12. For example, the low level controller 52 provides instructions to actuate the movement platform to move the robot 12. The low level controller 52 may receive movement instructions from the high level controller 50. The movement instructions may be received as movement commands from the remote control station. Although two controllers are shown, it is to be understood that the robot 12 may have one controller controlling the high and low level functions.

The various electrical devices of the robot 12 may be powered by a battery(ies) 104. The battery 104 may be recharged by a battery recharger station 106 (see also FIG. 1). The low level controller 52 may include a battery control circuit 108 that senses the power level of the battery 104. The low level controller 52 can sense when the power falls below a threshold and then send a message to the high level controller 50. The high level controller 50 may include a power management software routine that causes the robot 12 to move so that the battery 104 is coupled to the recharger 106 when the battery power falls below a threshold value. Alternatively, the user can direct the robot 12 to the battery recharger 106. Additionally, the battery 104 may be replaced or the robot 12 may be coupled to a wall power outlet by an electrical cord (not shown).

Figure 4:
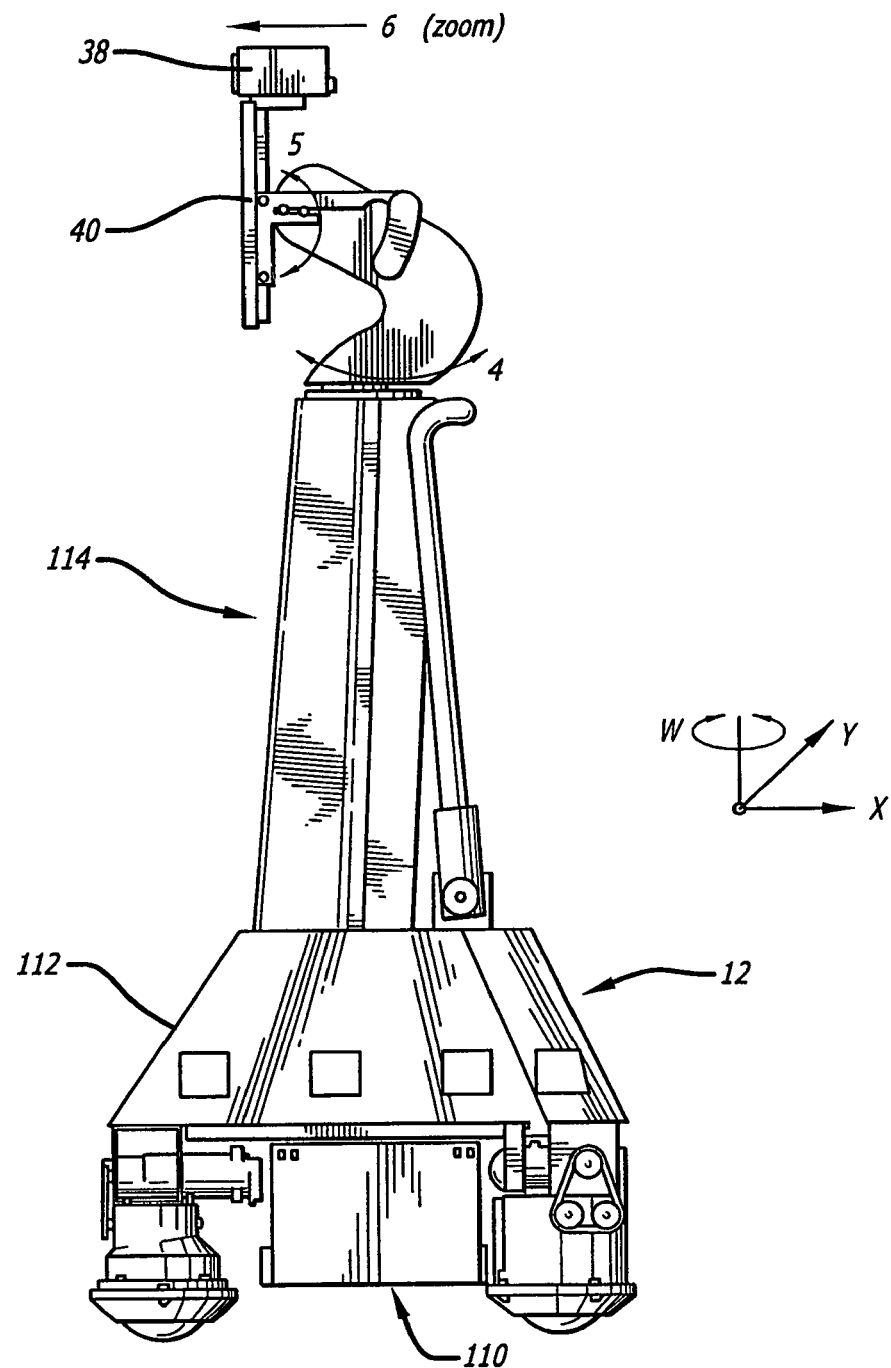
FIG. 4 is side view of the robot.

FIG. 4 shows an embodiment of the robot 12. The robot 12 may include a holonomic platform 110 that is attached to a robot housing 112. The holonomic platform 110 provides three degrees of freedom to allow the robot 12 to move in any direction.

The robot 12 may have an pedestal assembly 114 that supports the camera 38 and the monitor 40. The pedestal assembly 114 may have two degrees of freedom so that the camera 26 and monitor 24 can be swiveled and pivoted as indicated by the arrows.

Figure 5:
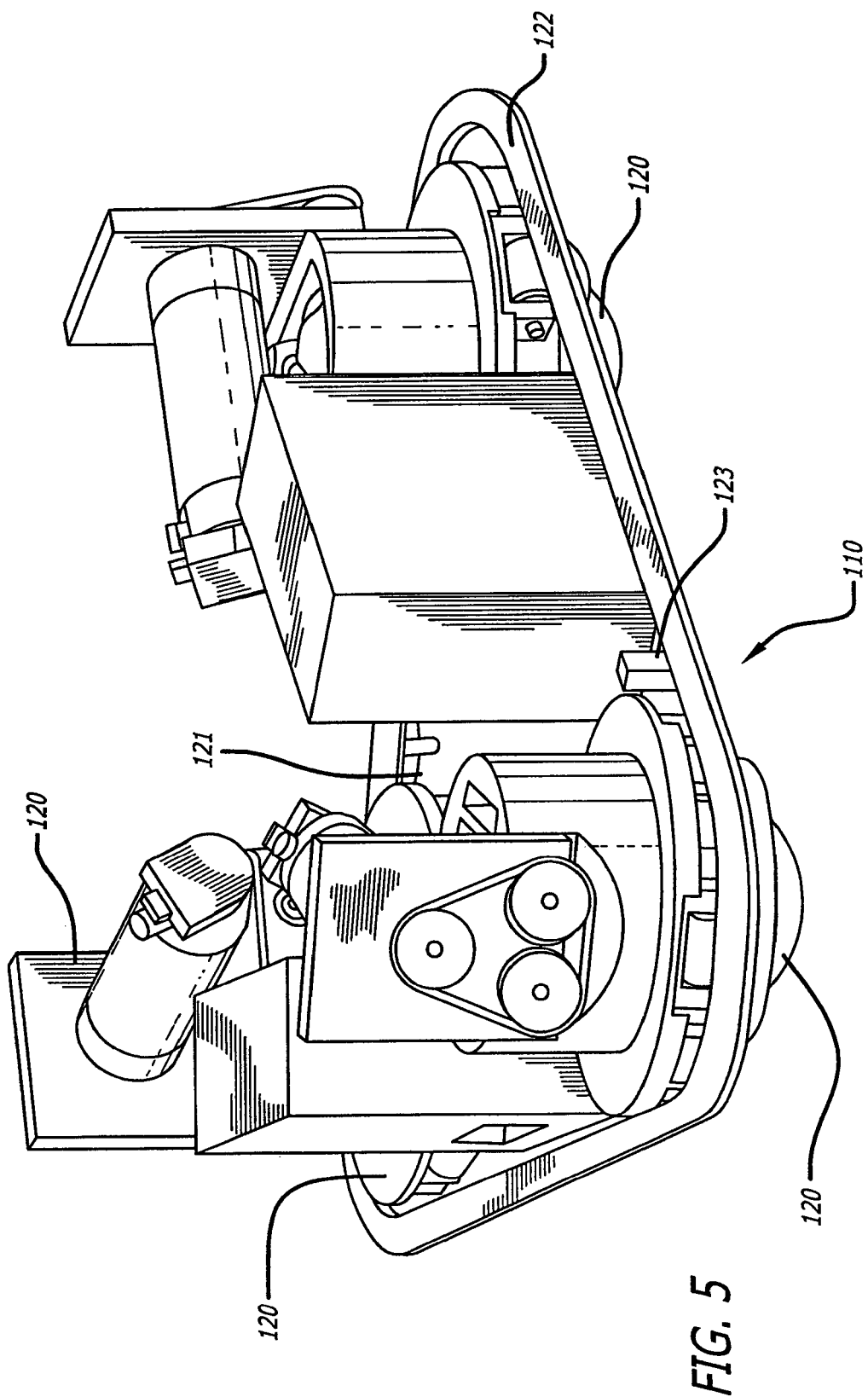
FIG. 5 is a top perspective view of a holonomic platform of the robot.

As shown in FIG. 5 the holonomic platform 110 may include three roller assemblies 120 that are mounted to a base plate 121. The roller assemblies 120 are typically equally spaced about the platform 110 and allow for movement in any direction, although it is to be understood that the assemblies may not be equally spaced.

The robot housing 112 may include a bumper 122. The bumper 122 may be coupled to optical position sensors 123 that detect when the bumper 122 has engaged an object. After engagement with the object the robot can determine the direction of contact and prevent further movement into the object.

Figure 6:
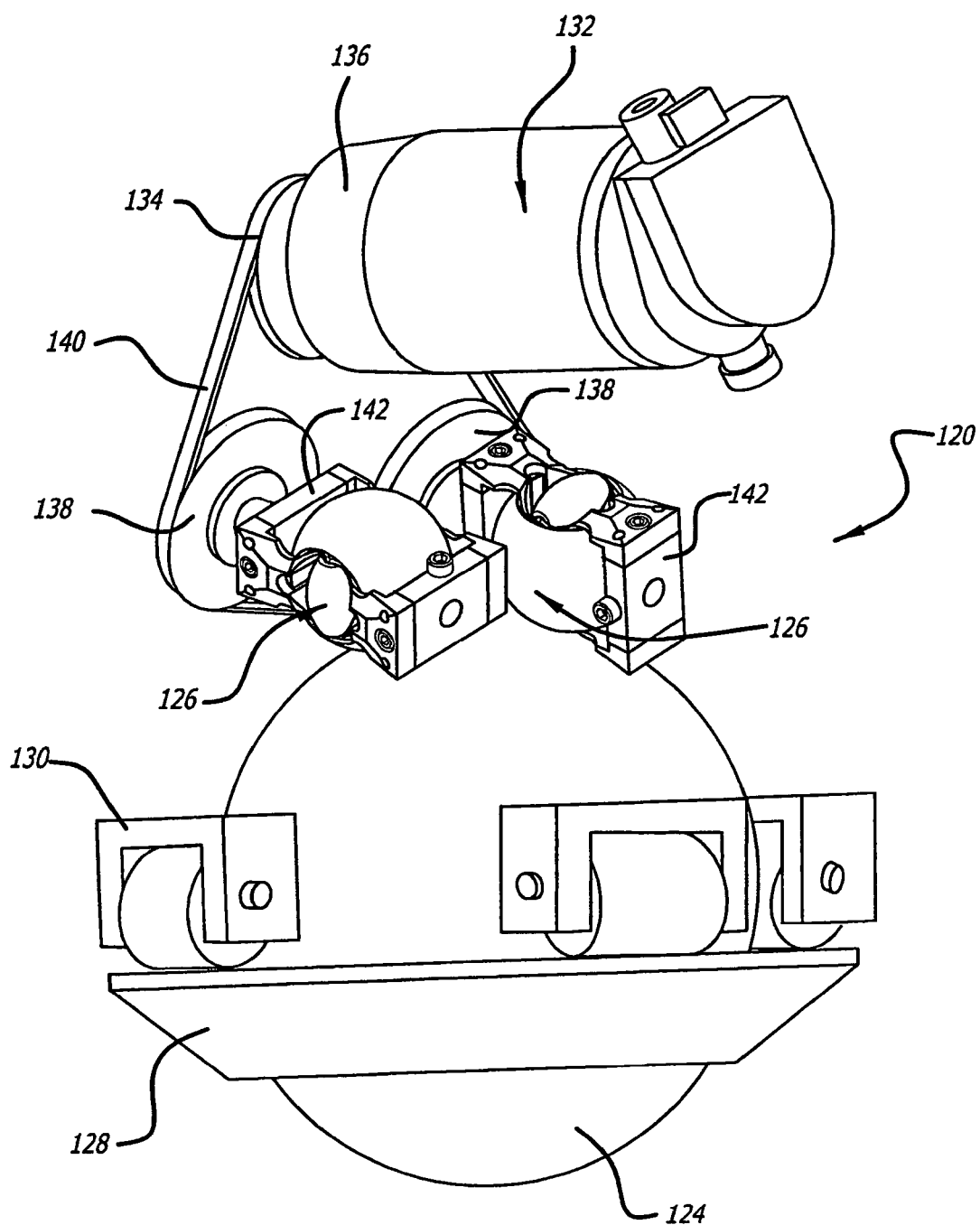
FIG. 6 is a side perspective view of a roller assembly of the holonomic platform.

FIG. 6 shows an embodiment of a roller assembly 120. Each assembly 120 may include a drive ball 124 that is driven by a pair of transmission rollers 126. The assembly 120 may include a retainer ring 128 and a plurality of bushings 130 that captures and allows the ball 124 to rotate in an x and y direction but prevents movement in a z direction. The assembly also holds the ball under the transmission rollers 126.

The transmission rollers 126 are coupled to a motor assembly 132. The assembly 132 corresponds to the motor 88 shown in FIG. 3. The motor assembly 132 includes an output pulley 134 attached to a motor 136. The output pulley 134 is coupled to a pair of ball pulleys 138 by a drive belt 140. The ball pulleys 138 are each attached to a transmission bracket 142. The transmission rollers 126 are attached to the transmission brackets 142.

Rotation of the output pulley 134 rotates the ball pulleys 138. Rotation of the ball pulleys 138 causes the transmission rollers 126 to rotate and spin the ball 124 through frictional forces. Spinning the ball 124 will move the robot 12. The transmission rollers 126 are constructed to always be in contact with the drive ball 124. The brackets 142 allow the transmission rollers 126 to freely spin and allow orthogonal directional passive movement of 124 when one of the other roller assemblies 120 is driving and moving the robot 12.

Figure 7:
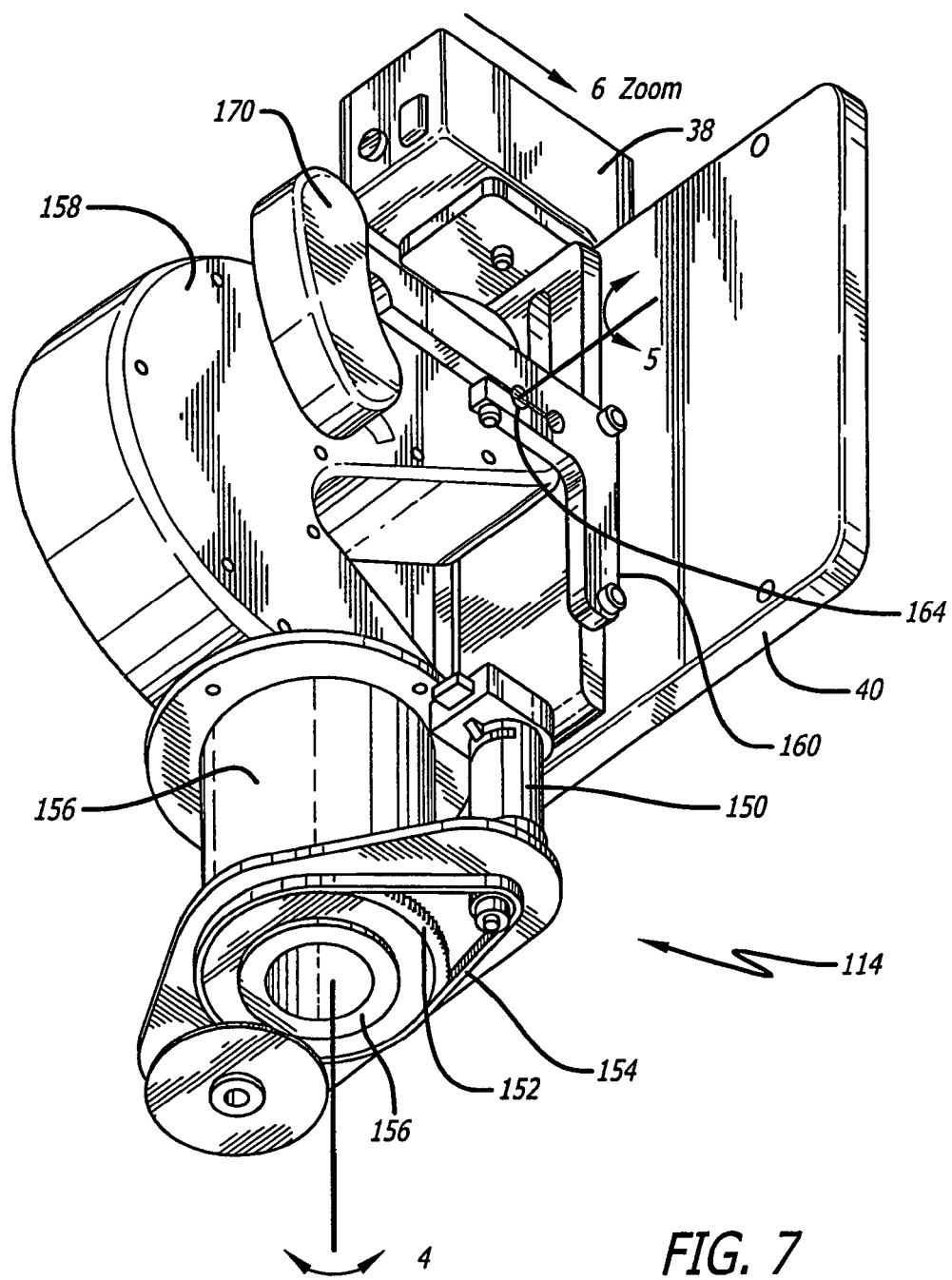
FIG. 7 is a bottom perspective view showing a pedestal assembly of the robot.

As shown in FIG. 7, the pedestal assembly 114 may include a motor 150 that is coupled to a gear 152 by a belt 154. The gear 152 is attached to a shaft 156. The shaft 156 is attached to an arm 158 that is coupled to the camera 38 and monitor 40 by a bracket 160. Activation of the motor 150 rotates the gear 152 and sleeve 156, and causes the camera 38 and monitor 40 to swivel (see also FIG. 4) as indicated by the arrows 4.

Figure 8:
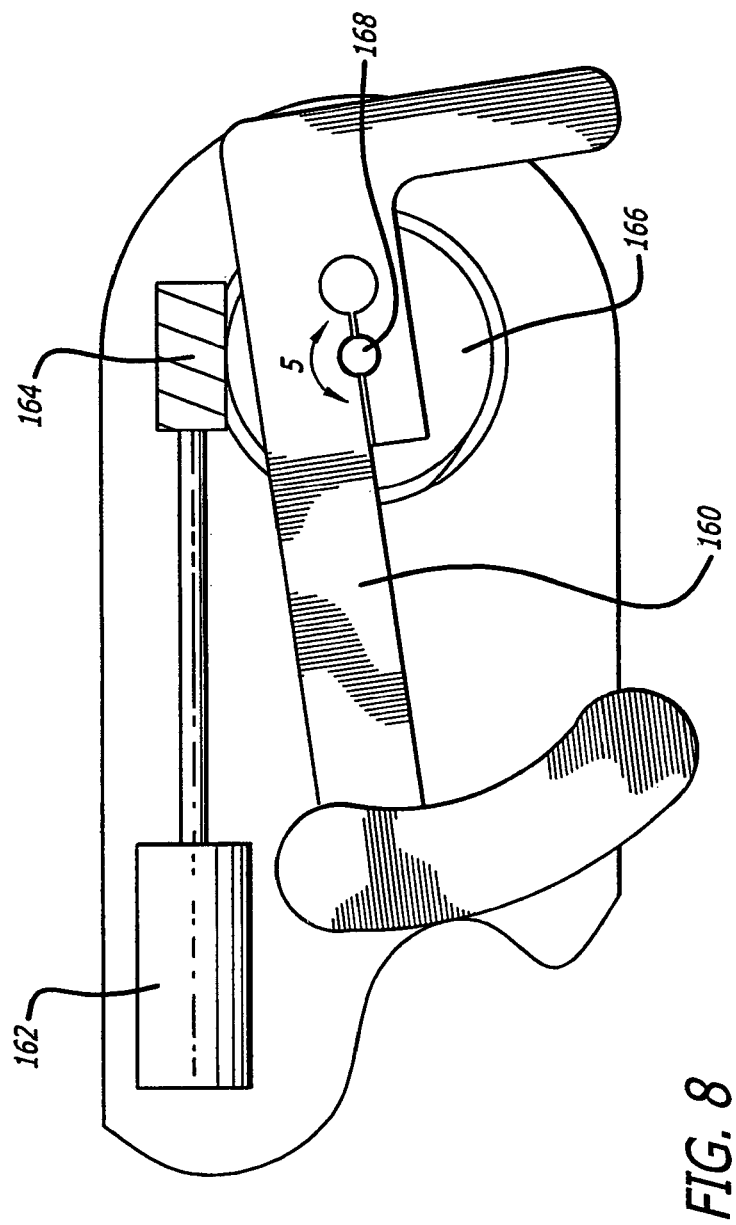
FIG. 8 is a sectional view showing an actuator of the pedestal assembly.

As shown in FIG. 8, the assembly 114 may further include a tilt motor 162 within the arm 158 that can cause the monitor 40 and camera 38 to pivot as indicated by the arrows 5. The tilt motor 162 may rotate a worm 164 that rotates a worm gear 166. The pin 168 is rigidly attached to both the worm gear 166 and the bracket 160 so that rotation of the gear 166 pivots the camera 38 and the monitor 40. The camera 38 may also include a zoom feature to provide yet another degree of freedom for the operator.

In operation, the robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home or facility by manipulating the input device 32 at a remote station 16.

Figure 9:
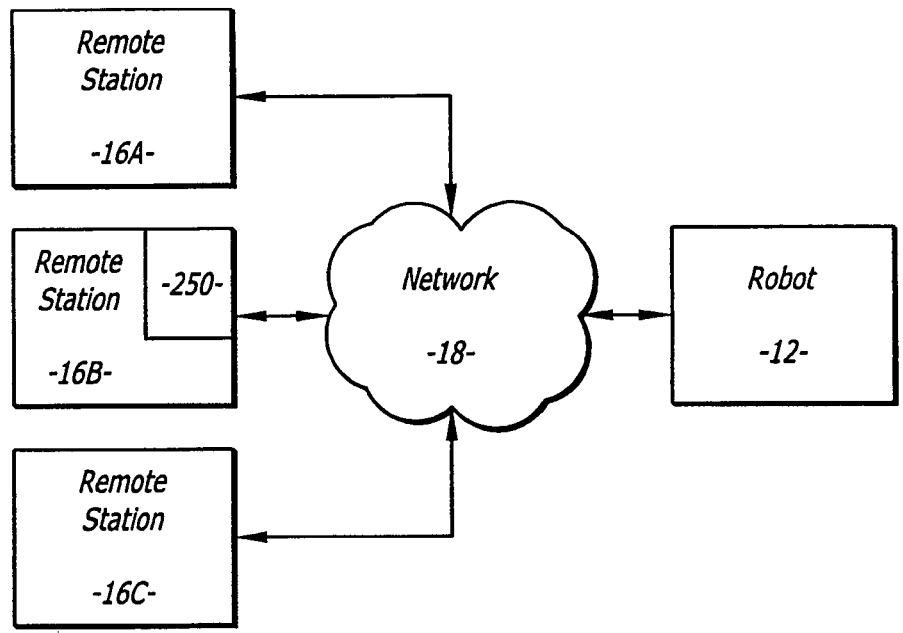
FIG. 9 is a schematic of a robotic system wherein multiple remote stations are coupled to the robot.

FIG. 9 shows a plurality of remote stations 16A-C that can access a robot 12 through a network 18. One of the remote stations 12B can be designated a master station which contains an arbitrator 250. The remote stations 16 may be configured so that all messages, commands, etc. provided to the robot 12 are initially routed to the master remote station 16B. Each message packet may include a priority field that contains the priority number of the station 16A, 16B or 16C sending the message. The arbitrator 250 determines which station has priority and then forwards the message from that station 16A, 16B or 16C to the robot 12. The arbitrator 250 may also send a call back message to the other remote station(s) stating that the station(s) with lower priority does not have access to the robot 12. The arbitrator 250 can cut-off access to the robot from one station and provide access to another station with a higher priority number.

Alternatively, a remote station may route a message, command, etc. to the robot 12 which then forwards a message, command, etc. to the arbitrator 250 to determine whether the station should have access. The arbitrator 250 can then provide a reply message either granting or denying access to the robot.

Figure 10:
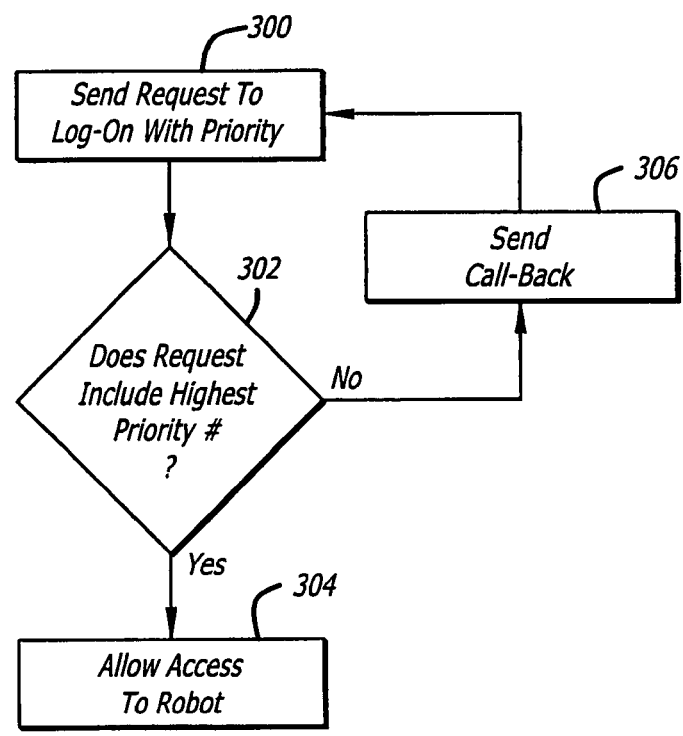
FIG. 10 is a flowchart showing an arbitration scheme for allowing access to the robot.

FIG. 10 shows a flowchart describing a process for access the robot 12. A remote station 16A, 16B or 16C may generate a request message to access the robot in block 300. The message may include the priority number of the remote station. The arbitrator 250 determines whether the request includes a priority number higher than any existing priority number in decision block 302. If a remote station has the same priority number the station first in time maintains access to the robot.

If the request included the highest priority number the arbitrator allows access to the robot in block 304. If the request does not contain the highest priority number, then arbitrator 250 sends a call-back message in block 306. To establish priority, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

Message packets may be transmitted between a robot 12 and a remote station 16. The packets provide commands and feedback. Each packet may have multiple fields. By way of example, a packet may include an ID field a forward speed field, an angular speed field, a stop field, a bumper field, a sensor range field, a configuration field, a text field and a debug field.

The identification of remote users can be set in an ID field of the information that is transmitted from the remote control station 16 to the robot 12. For example, a user may enter a user ID into a setup table in the application software run by the remote control station 16. The user ID is then sent with each message transmitted to the robot.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitrator may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables 1 and 2, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user<br>Notify requesting user that system is in use<br>Set timeout | Warn current user of pending user<br>Notify requesting user that system is in use<br>Set timeout = 5 m | Warn current user of pending user<br>Notify requesting user that system is in use<br>Set timeout = 5 m<br>Call back | Warn current user of pending user<br>Notify requesting user that system is in use<br>No timeout<br>Call back |
| | Caregiver | Warn current user of pending user.<br>Notify requesting user that system is in use.<br>Release control | Not Allowed | Warn current user of pending user<br>Notify requesting user that system is in use<br>Set timeout = 5 m<br>Queue or callback | Warn current user of pending user<br>Notify requesting user that system is in use<br>Set timeout = 5 m | Warn current user of pending user<br>Notify requesting user that system is in use<br>No timeout<br>Callback |
| | Doctor | Warn current user of pending user<br>Notify requesting user that system is in use<br>Release control | Warn current user of pending user<br>Notify requesting user that system is in use<br>Set timeout = 5 m | Warn current user of pending user<br>Notify requesting user that system is in use<br>No timeout<br>Callback | Notify requesting user that system is in use<br>No timeout<br>Queue or callback | Warn current user of pending user<br>Notify requesting user that system is in use<br>No timeout<br>Callback |
| | Family | Warn current user of pending user<br>Notify requesting user that system is in use<br>Release Control | Notify requesting user that system is in use<br>No timeout<br>Put in queue or callback | Warn current user of pending user<br>Notify requesting user that system is in use<br>Set timeout = 1 m | Warn current user of pending user<br>Notify requesting user that system is in use<br>Set timeout = 5 m<br>Queue or callback | Warn current user of pending user<br>Notify requesting user that system is in use<br>No timeout<br>Callback |
| | Service | Warn current user of pending user<br>Notify requesting user that system is in use<br>No timeout | Notify requesting user that system is in use<br>No timeout<br>Callback | Warn current user of request<br>Notify requesting user that system is in use<br>No timeout<br>Callback | Warn current user of pending user<br>Notify requesting user that system is in use<br>No timeout<br>Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

Figure 11:
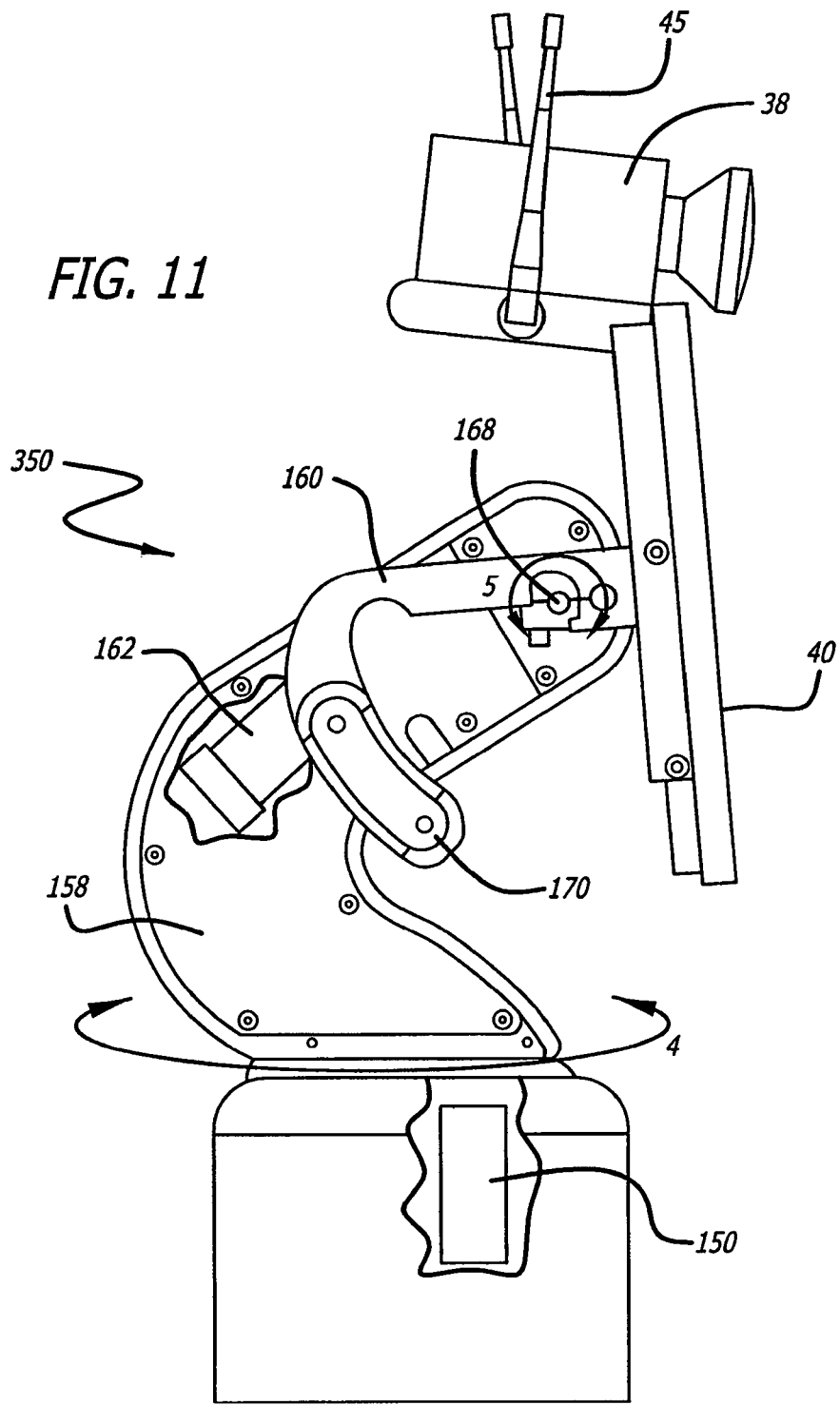
FIG. 11 is a side view of a robot head.

FIG. 11 shows a robot head 350 that can both pivot and spin the camera 38 and the monitor 40. The robot head 350 can be similar to the robot 12 but without the platform 110. The robot head 350 may have the same mechanisms and parts to both pivot the camera 38 and monitor 40 about the pivot axis 4, and spin the camera 38 and monitor 40 about the spin axis 5. The pivot axis may intersect the spin axis. Having a robot head 350 that both pivots and spins provides a wide viewing area. The robot head 350 may be in the system either with or instead of the mobile robot 12.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

For example, although the arbitrator is described and shown as being in one of the remote stations, the arbitrator could be within a server, robot or any device, that is connected to the network and in communication with both the remote stations and the robot.

What is claimed is:

1. A robot system, comprising:
   a robot that has a camera and a monitor;
   a first remote station that has a monitor and is configured to access and control said robot, said first remote station having a first input device operated by a first user to cause movement of said robot;
   a second remote station that has a monitor and is configured to access and control said robot, said second remote station having a second input device operated by a second user to cause movement of said robot; and,
   an arbitrator that can operate in an exclusive mode to control access and control movement of said robot exclusively by said first remote station or second remote station, said arbitrator provides a mechanism that allows said first remote station to exclusively access and control movement of said robot, said mechanism denies exclusive access to said robot by said second remote station and notifies the second user that exclusive access to said robot is denied, and subsequent to when access is denied notifies the second user that said robot can be exclusively accessed and controlled.

2. The system of claim 1, further comprising a broadband network coupled to said robot and said first and second remote stations.

3. The system of claim 2, wherein said first and second remote stations each have a priority and said arbitrator provides robot access to said remote station with a highest priority.

4. The system of claim 3, wherein said first and second remote stations may be given priority as a local user, a doctor, a caregiver, a family member, or a service user.

5. The system of claim 2, wherein said arbitrator sends a call back message to inform the user that said robot can be accessed.

6. A robot system, comprising:

a robot that has a camera and a monitor;

a first remote station that has a monitor and is configured to access and control said robot, said first remote station has a first input device operated by a first user to cause movement of said robot; and, a second remote station that has a monitor and is configured to and can access and control said robot, said second remote station has a second input device operated by a second user to cause movement of said robot; and, arbitration means for operating in an exclusive mode and for allowing exclusive access and control of said robot by said first remote station, denying exclusive access to said robot by said second remote station and notifying the second user of said denial, and informing the second user that was previously denied access to said robot, that said robot can be exclusively accessed and controlled.

7. The system of claim 6, further comprising a broadband network coupled to said robot and said first and second remote stations.

8. The system of claim 7, wherein said first and second remote stations each have a priority and said arbitrator provides robot access to said remote station with a highest priority.

9. The system of claim 8, wherein said first and second remote stations may be given priority as a local user, a doctor, a caregiver, a family member, or a service user.

10. The system of claim 7, wherein said arbitrator sends a call back message to inform the user that said robot can be accessed.

11. A method for controlling access to a remote controlled robot, comprising:

providing a robot that has a camera and a monitor;

providing a first remote station that has a monitor and is configured to access and control said robot, said first remote station has a first input device operated by a first user to cause movement of said robot;

providing a second remote station that has a monitor and is configured to access and control said robot, said second remote station has a second input device operated by a second user to cause movement of said robot;

exclusively accessing and controlling the robot by the first remote station;

denying with an arbitrator exclusive access to the robot by the second remote station and notifying the second user of such denial; and, informing with the arbitrator the second user of the second remote station that the robot can be exclusively accessed and controlled.

12. The method of claim 11, wherein the remote station is informed that the robot can be accessed with a call back message.

\* \* \* \* \*